(12) United States Patent
Shen et al.

(10) Patent No.: US 10,232,244 B2
(45) Date of Patent: Mar. 19, 2019

(54) MEASURING DEVICE AND MEASURING METHOD FOR PEDAL PLANE ANGLE OF BICYCLE

(71) Applicant: GIANT MANUFACTURING CO., LTD., Taichung (TW)

(72) Inventors: Chih-Hsiang Shen, Taichung (TW); Wei-chieh Ho, Taichung (TW); Chien-Hung Chen, Taichung (TW)

(73) Assignee: GIANT MANUFACTURING CO., LTD., Taichung (TW)

( * ) Notice: Subject to any disclaimer, the term of this patent is extended or adjusted under 35 U.S.C. 154(b) by 0 days.

(21) Appl. No.: 15/475,936

(22) Filed: Mar. 31, 2017

(65) Prior Publication Data

US 2017/0296896 A1    Oct. 19, 2017

(30) Foreign Application Priority Data

Apr. 18, 2016  (TW) .............................. 105111992 A

(51) Int. Cl.
| | |
|---|---|
| *A63B 69/16* | (2006.01) |
| *A63B 24/00* | (2006.01) |
| *G01B 5/24* | (2006.01) |
| *A61B 5/107* | (2006.01) |
| *A61B 5/22* | (2006.01) |
| *A61B 5/00* | (2006.01) |

(Continued)

(52) U.S. Cl.
CPC ............ *A63B 69/16* (2013.01); *A61B 5/1071* (2013.01); *A61B 5/221* (2013.01); *A61B 5/4561* (2013.01); *A63B 24/0006* (2013.01); *B62M 3/00* (2013.01); *B62M 3/08* (2013.01); *G01B 5/24* (2013.01); *A63B 2024/0015* (2013.01); *A63B 2220/44* (2013.01); *A63B 2220/51* (2013.01); *A63B 2220/803* (2013.01); *B62K 2207/00* (2013.01)

(58) Field of Classification Search
CPC .. G01L 1/00; A61B 5/22; A61B 22/06; G01B 7/16; G01D 9/00
See application file for complete search history.

(56) References Cited

U.S. PATENT DOCUMENTS 4,423,630 A *   1/1984  Morrison ............... A61B 5/221
                                                          340/323 R
8,011,242 B2 *  9/2011  O'Neill .................... G01L 3/242
                                                            73/379.01

(Continued)

*Primary Examiner* — Jewel V Dowtin
(74) *Attorney, Agent, or Firm* — Muncy, Geissler, Olds & Lowe, P.C.

(57) ABSTRACT

A measuring device for a pedal plane angle of a bicycle includes a pedal body, an angle sensing unit and a central processing unit (CPU). The angle sensing unit is disposed in an accommodating chamber of the pedal body, and senses an angle of the pedal body to send an angle sensing signal. The CPU analyzes the angle sensing signal to obtain angle data of the pedal body relative to an angle of a reference plane to accordingly learn an angle relationship between the pedal body and the reference plane. The angle relationship may coordinate with other sensing units, for example, data of a pedaling force sensing unit to mutually correct and analyze the data, so as to obtain correct pedaling force information. With the angle data, whether a pedaling angle of a rider is correct can be learned to prevent sports injuries caused by incorrect pedaling angles.

14 Claims, 10 Drawing Sheets

(51) Int. Cl.
*B62M 3/00* (2006.01)
*B62M 3/08* (2006.01)

(56) References Cited

U.S. PATENT DOCUMENTS

| | | | | |
|---|---|---|---|---|
| 8,327,723 | B2* | 12/2012 | Roudergues | G01L 5/225 |
| | | | | 73/760 |
| 8,584,520 | B2* | 11/2013 | Kokkoneva | G01D 11/24 |
| | | | | 73/379.01 |
| 8,584,529 | B2* | 11/2013 | Fisher | B62M 3/00 |
| | | | | 73/760 |
| 8,689,645 | B2 | 4/2014 | Watarai | |
| 9,551,623 | B2* | 1/2017 | Biermann | A63B 24/0062 |
| 2012/0214646 | A1* | 8/2012 | Lull | G01L 3/242 |
| | | | | 482/5 |

* cited by examiner

MEASURING DEVICE AND MEASURING METHOD FOR PEDAL PLANE ANGLE OF BICYCLE

FIELD OF THE INVENTION

The present invention relates to a measuring device, and particularly to a measuring device and a measuring method for a pedal plane angle of a bicycle.

BACKGROUND OF THE INVENTION

As times continue to change, bicycles have transformed from transportation means to entertainment and workout tools of the modern people. Along with the progressing technologies, a bicycle may be installed with numerous sensors, which allow a rider to record riding data such as the pedaling speed, riding mileage, pedaling frequency and pedaling force while the rider rides the bicycle. Through data analysis, the rider may learn his/her physical conditions.

For example, the U.S. Pat. No. 8,689,645, "Bicycle Crank Arm", discloses a bicycle incorporating a pedaling force sensor. The disclosure includes a crank body, a reference member and a sensor. The reference member is attached to the crank body. The sensor is attached to at least one of the crank body and the reference member. When the rider pedals, the crank body receives the force and becomes curved to cause a change in the distance between the crank body and the reference member, hence obtaining the size of the pedaling force.

Further, in known technologies, a sensor may be used to detect an angular position of a pedal on a circular motion. In conjunction with the distance between the crank body and the reference member, the size of the pedaling force and the relationship between the pedaling force and the pedaling position may be calculated, so as to provide a training reference for adjusting the pedaling force for the bicycle rider.

When the pedal is pedaled based on the foregoing method, corrections are made according to the angular position of the pedal performing a circular motion and the force applied on the crank body. It should be noted that, a force is applied by the user upon the pedal of the bicycle in a circular manner, and the tangential direction of the circumference in fact accounts as an effective force. In known technologies, the measurement of the angle of the pedal plane of the pedal is overlooked, in a way that the real effective pedaling force of the rider cannot be truly calculated. Further, to satisfy a sense of accomplishment, a rider may usually value more highly on the riding mileage and riding speed, and neglect whether the pedaling angle, which is the most important, is accurate. Over an extended period of time, sports injuries of the feet or other parts may likely be caused, resulting in reduced riding efficiency. Therefore, there is a need for a solution that detects an angle relationship between a pedal plane and the ground surface to calculate a real pedaling force and to reduce sports injuries.

SUMMARY OF THE INVENTION

It is a primary object of the present invention to solve issues of the incapability of calculating an angle relationship between a pedal plane and the ground surface, sports injuries easily caused and reduced riding efficiency, and the incapability of calculating a real pedaling force.

To achieve the above object, the present invention provides a measuring device for a pedal plane of a bicycle. The measuring device is pivotally connected to a mandrel and includes a pedal body, an angle sensing unit and a central processing unit (CPU). The pedal body includes a pivoting portion for pivotally connecting to the mandrel, a pedal plane, and an accommodating chamber, in which the angle sensing unit is disposed. The CPU is electrically connected to the angle sensing unit. The angle sensing unit senses an angle of the pedal body and sends an angle sensing signal. The CPU receives and analyzes the angle sensing signal to obtain angle data of the pedal body relative to an angle of a reference plane.

To achieve the above object, the present invention further provides a measuring method for a pedal plane of a bicycle. The measuring method includes following steps.

In step S1, an angle of a pedal body is sensed by an angle sensing unit disposed on the pedal body to send an angle sensing signal.

In step S2, the angle sensing signal is analyzed by a CPU to obtain angle data of the pedal body relative to an angle of a reference plane.

In conclusion, the present invention provides following features.

Using the angle sensing unit and the CPU, the angle data of the pedal body relative to the angle of the reference plane is obtained. Thus, it may be learned whether a pedaling angle during riding is correct to reduce sports injuries.

Further, the angle data may coordinate with other sensing units and be mutually corrected to obtain accurate value information. For example, the angle data may coordinate with a pedal sensing unit to be mutually corrected and analyzed to obtain correct pedaling force information.

DETAILED DESCRIPTION OF THE PREFERRED EMBODIMENTS

Figure 1:
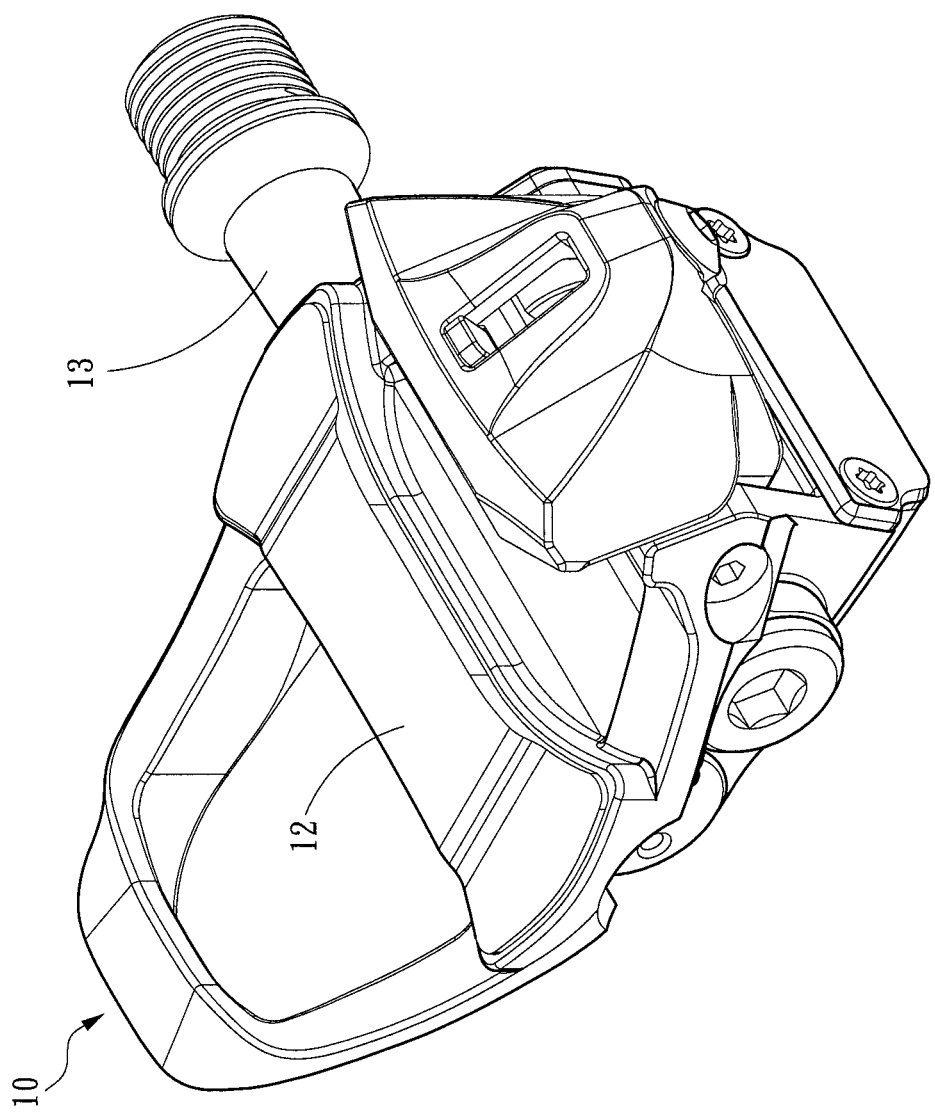
FIG. 1 is a perspective structural schematic diagram according to a first embodiment of the present invention.
Figure 2:
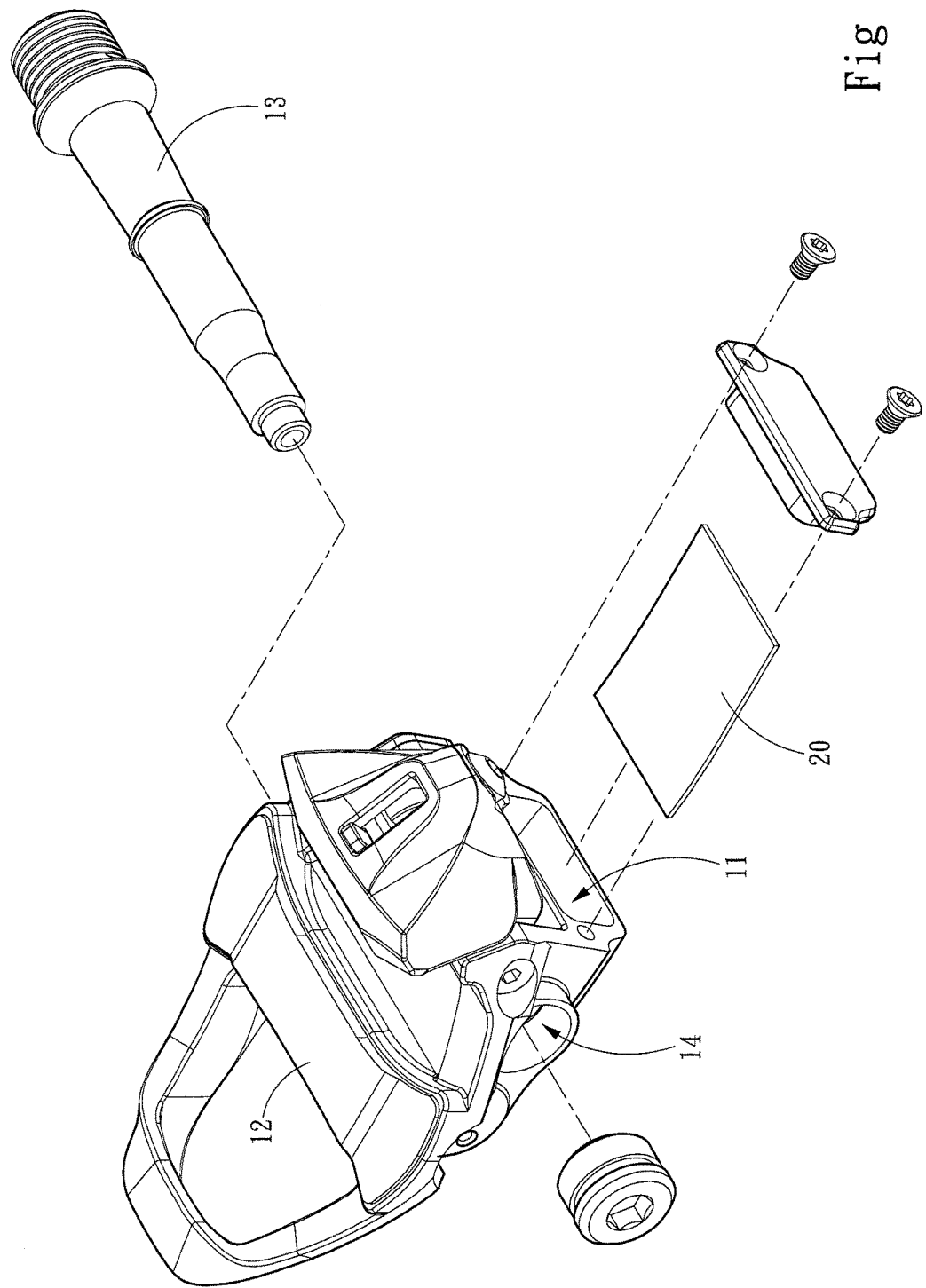
FIG. 2 is an exploded partial schematic diagram according to the first embodiment of the present invention.
Figure 3:
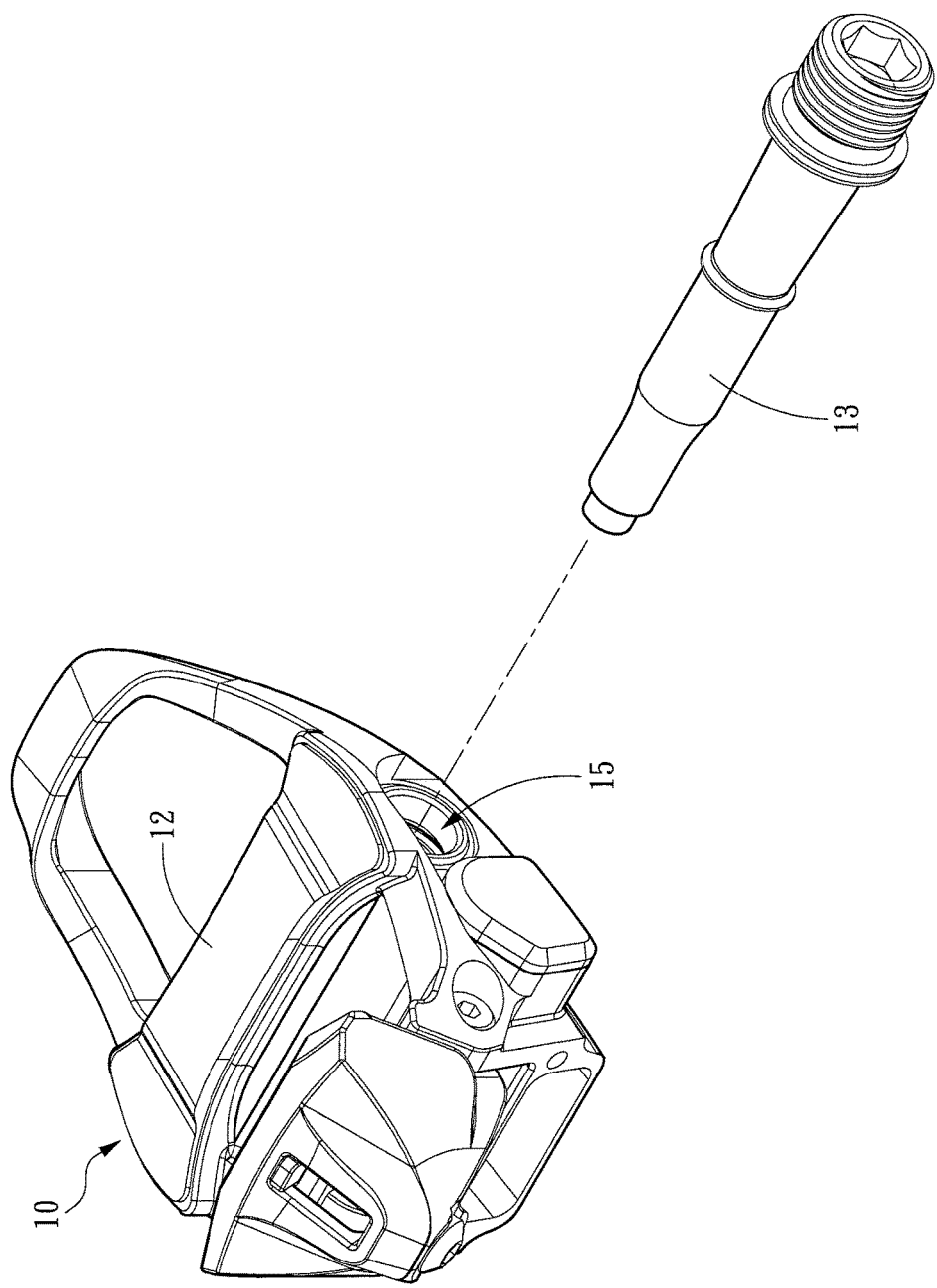
FIG. 3 is an exploded partial schematic diagram of another aspect according to the first embodiment of the present invention.

Details and technical contents of the present invention are given with the accompanying drawings below.

Referring to FIG. 1 to FIG. 4, the present invention provides a measuring device for a pedal plane angle of a bicycle. The measuring device for a pedal plane of a bicycle of the present invention is pivotally connected to a mandrel 13 and includes a pedal body 10, an angle sensing unit 20 and a central processing unit (CPU) 30. The angle sensing unit 20 is disposed in an accommodating chamber 11 of the pedal body 10. In the present invention, the pedal body 10 further includes a pivoting portion 15 for pivotally connecting to the mandrel 13, a pedal plane 12, and a battery slot 14. The mandrel 13 and the battery slot 14 are provided between the pedal plane 12 and the accommodating chamber 11. The mandrel 13 is connected to a crank (not shown) to rotate. The battery slot 14 holds a power element for powering the angle sensing unit 20 and the CPU 30. For example, the battery slot 14 may accommodate a common dry cell, or may be designed to hold batteries of other sizes, e.g., lithium batteries.

Figure 5:
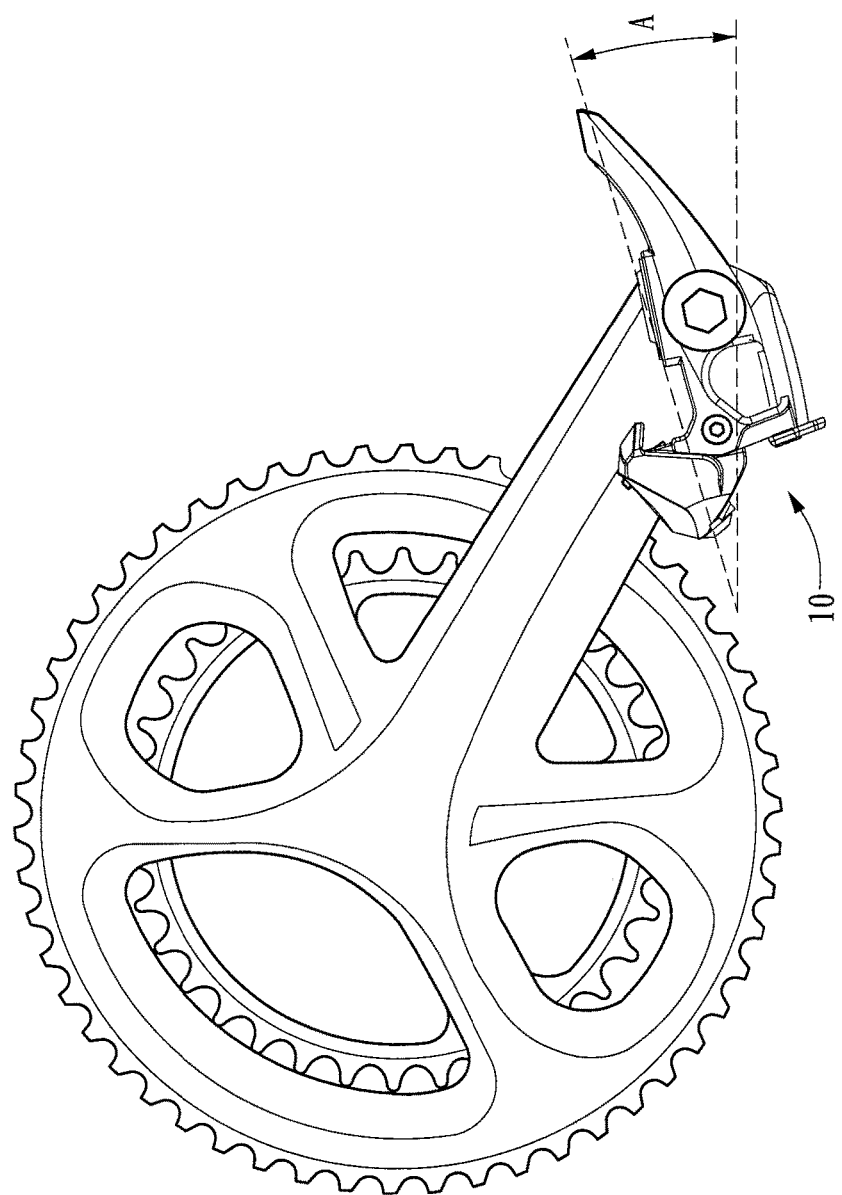
FIG. 5 is a schematic diagram of a pedaling angle according to the first embodiment of the present invention.

Referring to FIG. 5, when a rider rides the bicycle, the angle sensing unit 20 senses an angle A of the pedal body 10 and sends an angle sensing signal. The CPU 30 analyzes the angle sensing signal to obtain angle data of the pedal body 10 relative to an angle A of a reference plane. For example, the reference plane is generally a horizontal plane, or may be modified according to different requirements. For example, the angle sensing unit 20 may be at least one selected from a group consisting of an accelerometer, a gyroscope and an angle sensor. The accelerometer calculates accelerations of two directions to obtain the angle change. The gyroscope obtains the angle change through the angular momentum of a rotating rotor located at the mandrel. The angle sensor, by arranging a vertical detection plane of a chip perpendicular to the mandrel of a magnet, detects the rotational direction. For example but not limited to, the gyroscope and the angle sensor may be incorporated to achieve multi-axial sensing to increase the sensing accuracy.

Figure 4:
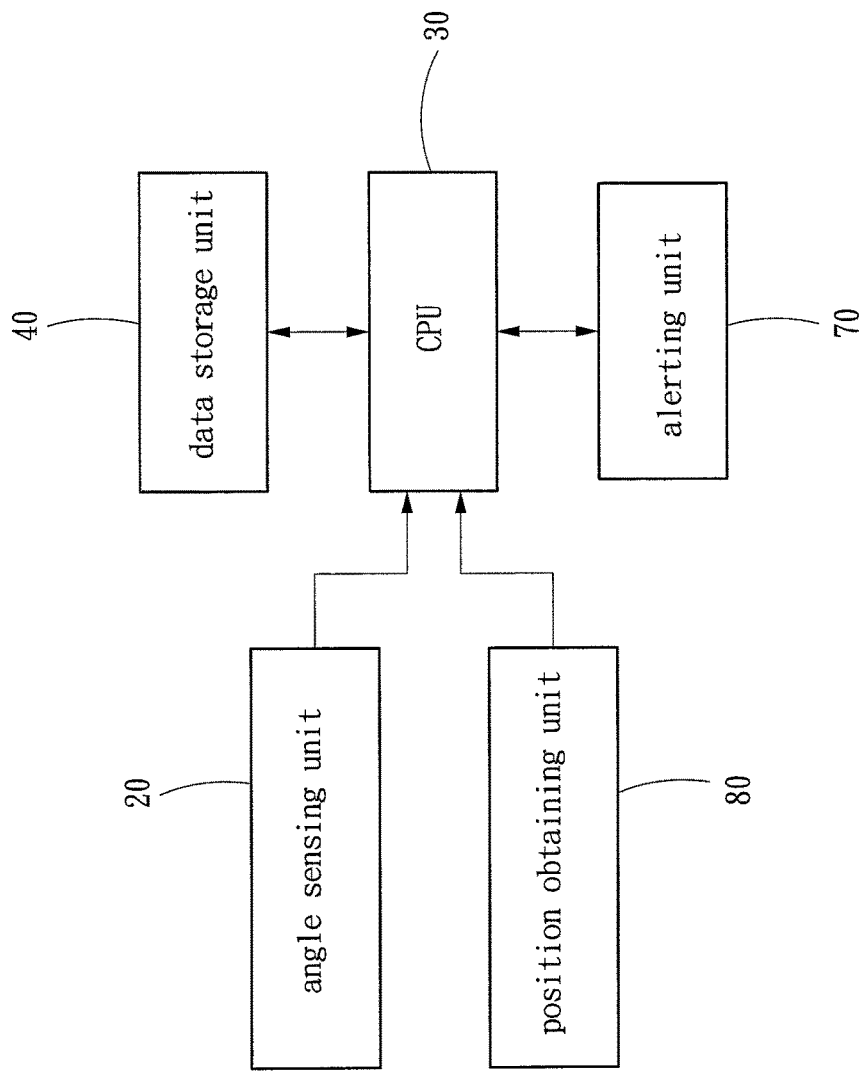
FIG. 4 is a function block diagram according to a first embodiment of the present invention.

Referring to FIG. 4, the embodiment further includes a position obtaining unit 80, an alerting unit 70 and a data storage unit 40. The position obtaining unit 80 is electrically connected to the CPU 30, and is capable of sending position data according to a position of the pedal body 10 performing a circular motion to the CPU 30. The CPU 30 combines the angle data and the position data to obtain pedaling motion information. The data storage unit 40 is electrically connected to the CPU 30, and stores the angle data, the position data and the pedaling motion information for the rider to output to an external device after riding. Thus, the rider may inspect whether his/her pedal angle is correct to prevent sports injuries and to enhance riding efficiency. The alerting unit 70 is also electrically connected to the CPU 30. During riding, if the pedal angle of the rider is incorrect, the alerting unit 70 detects the angle data as being abnormal, and issues an alert to notify the rider to pay attention to the pedaling posture. For example, the alert may be flashing, beeping or other means that causes the attention of the rider. In the embodiment, the CPU 30, the position obtaining unit 80, the alerting unit 70 and the data storage unit 40 are all disposed in the accommodating chamber 11.

Figure 6:
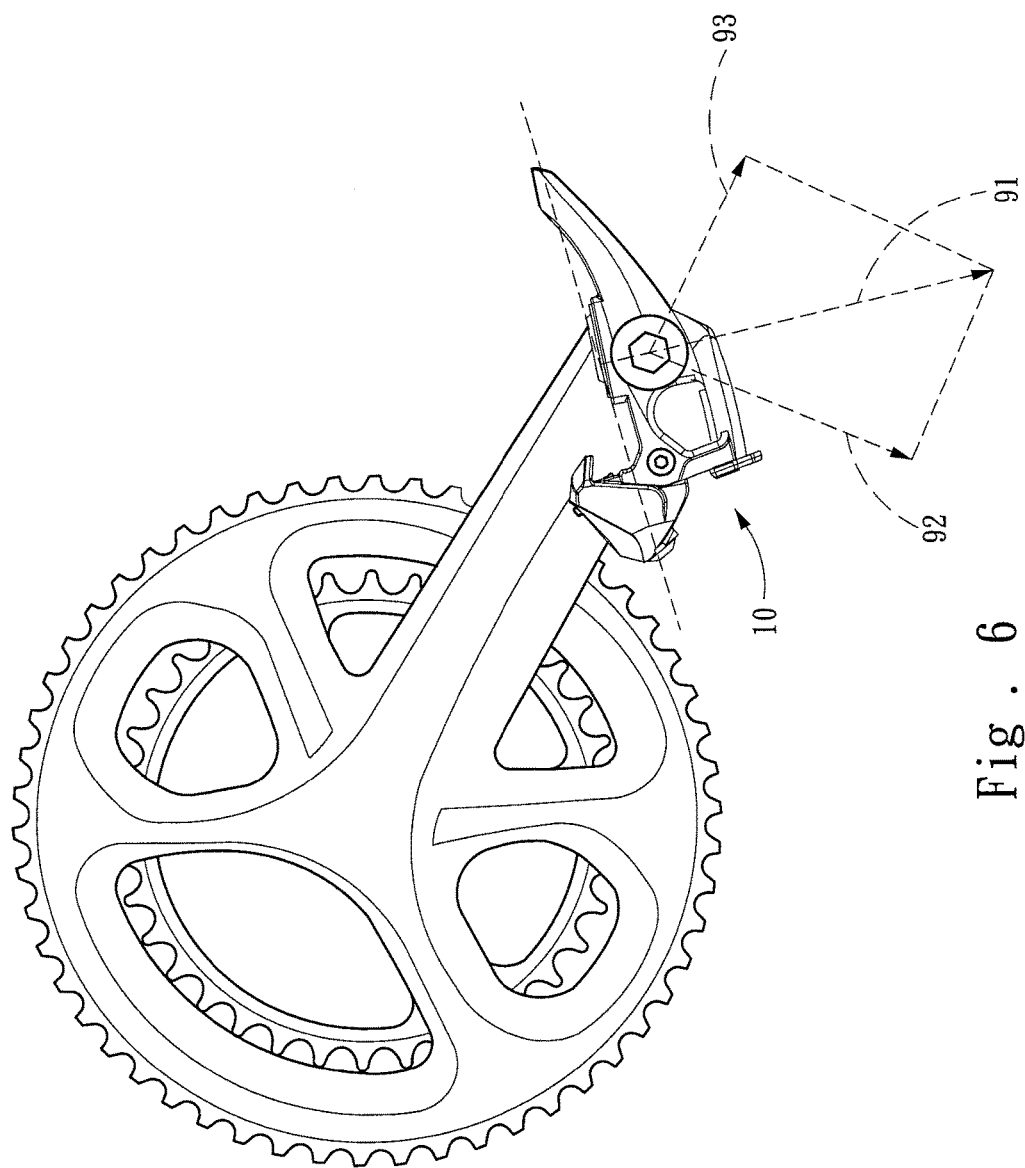
FIG. 6 is a schematic diagram of a force application direction according to the first embodiment of the present invention.

As shown in FIG. 5 and FIG. 6, the angle sensing unit 20 senses the pedal plane of the pedal body 10 and the angle A of the reference plane to obtain a force application direction 91 perpendicular to the pedal plane of the pedal body 10. Further with the position of the circular motion obtained by the position obtaining unit 80, an effective force application direction 91 along the tangential direction and an ineffective force application direction 93 along the normal line of the circumference are obtained. With the obtained effective force application direction 92, the pedaling angle of the rider may be corrected to maximize of the result of the pedaling force.

The obtained angle data may coordinate with other data and be mutually corrected. For example but not limited to, the angle data may be mutually corrected with data of a pedal sensing unit to obtain a correct pedaling force. However, the angle data may be coordinate with other sensing units in addition to the above example.

Figure 7:
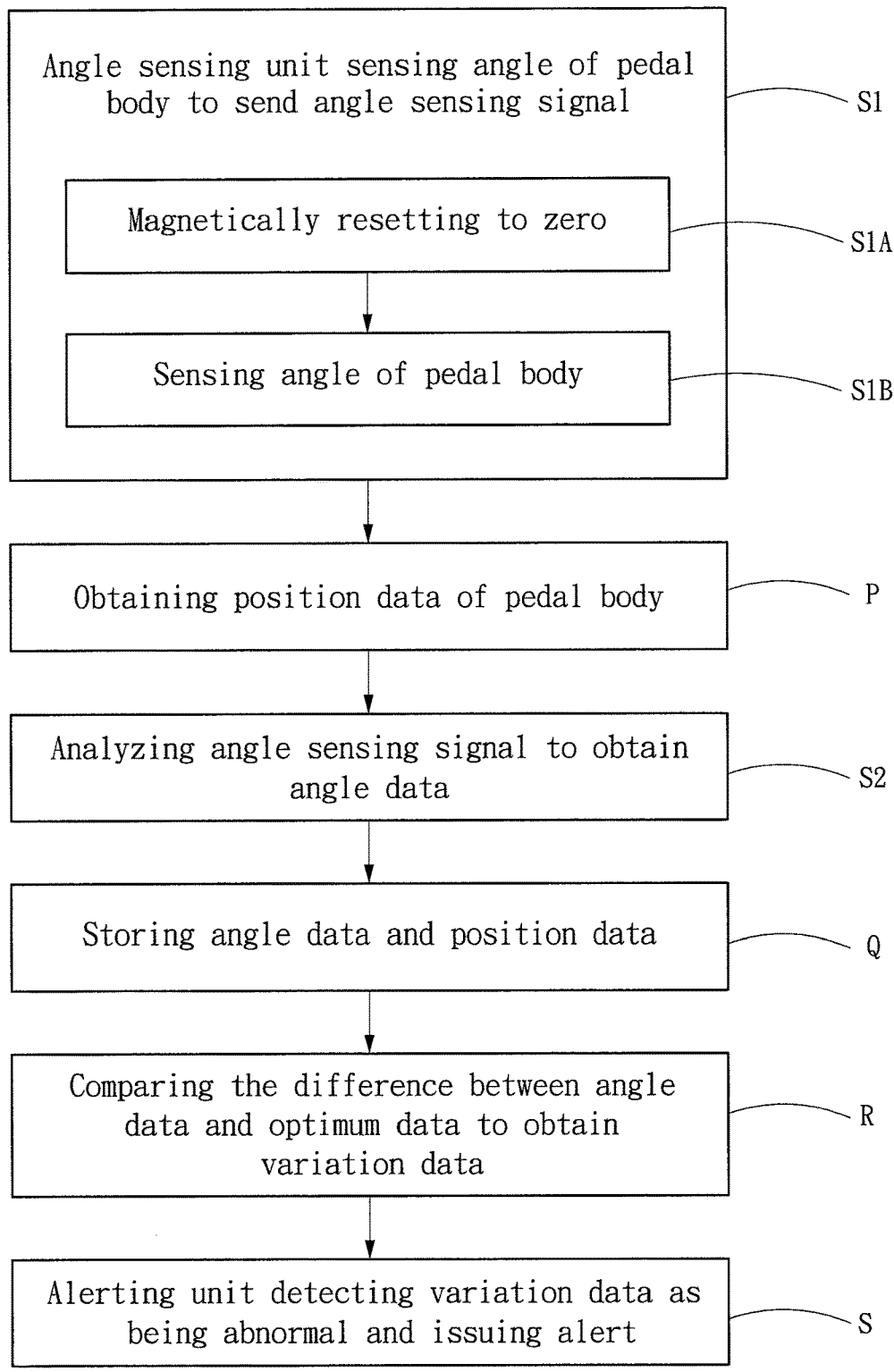
FIG. 7 is a schematic diagram of a process according to the first embodiment of the present invention.

Referring to FIG. 7, a measuring method for a pedal plane angle of a bicycle according to an embodiment includes following steps.

In step S1, an angle of a pedal body 10 is sensed by an angle sensing unit 20 disposed on the pedal body 10 to send an angle sensing signal. In the embodiment, step S1 further includes following steps.

In step S1A, the angle sensing unit 20 is magnetically reset to zero in response to magnetic differences in different regions. To magnetically reset the angle sensing unit 20 to zero, the angle sensing unit 20 is moved along a track of the numeral 8 in the air. Other types of angle sensing units 20 may have respectively resetting methods, and such are omitted herein.

In step S1B, the angle of the pedal body 10 is sensed by the angle sensing unit 20 to send the angle sensing signal.

After step S1, the measuring method further includes following steps.

In step P, when the pedal body 10 performs a circular motion, position data of a position of the pedal body 10 performing the circular motion is obtained by a position obtaining unit 80.

In step S2, the angle sensing signal is analyzed by a CPU 30 to obtain angle data of the pedal body 10 relative to an angle of a reference plane, and the angle data is coordinated with the position data to obtain pedaling motion information.

In step Q, the angle data, the position data and the pedaling motion information is stored in a data storage unit 40 for the rider to view after riding and to inspect whether his/her pedaling angle is correct.

In step R, the CPU 30 compares the difference between the angle data and an optimum data to obtain a variation data. The optimum data is according to the consideration of ergonomics and the most effective riding angle.

In step S, when the alerting unit 70 detects the variation data as being abnormal, the alerting unit 70 issues an alert to notify the rider.

Figure 8:
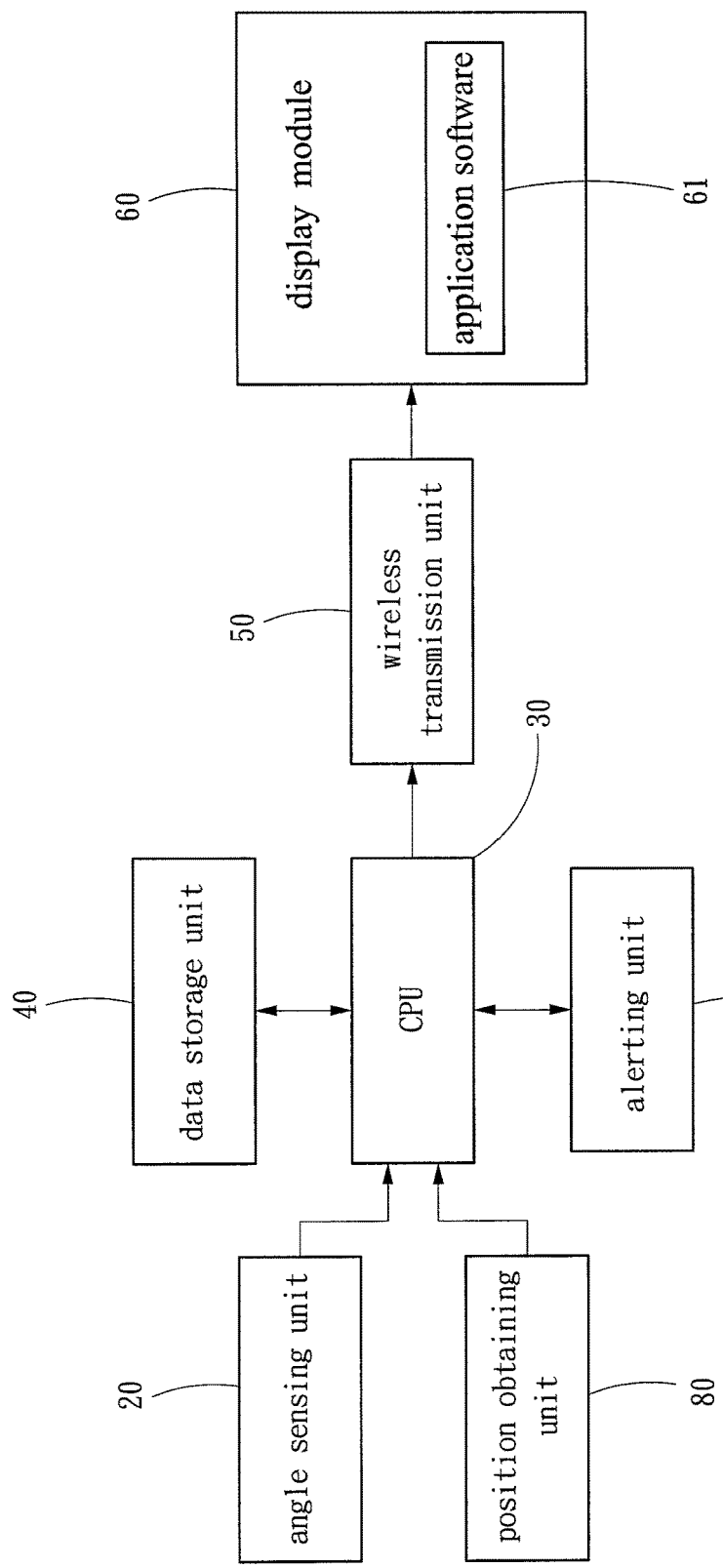
FIG. 8 is a function block diagram according to a second embodiment of the present invention.
Figure 9:
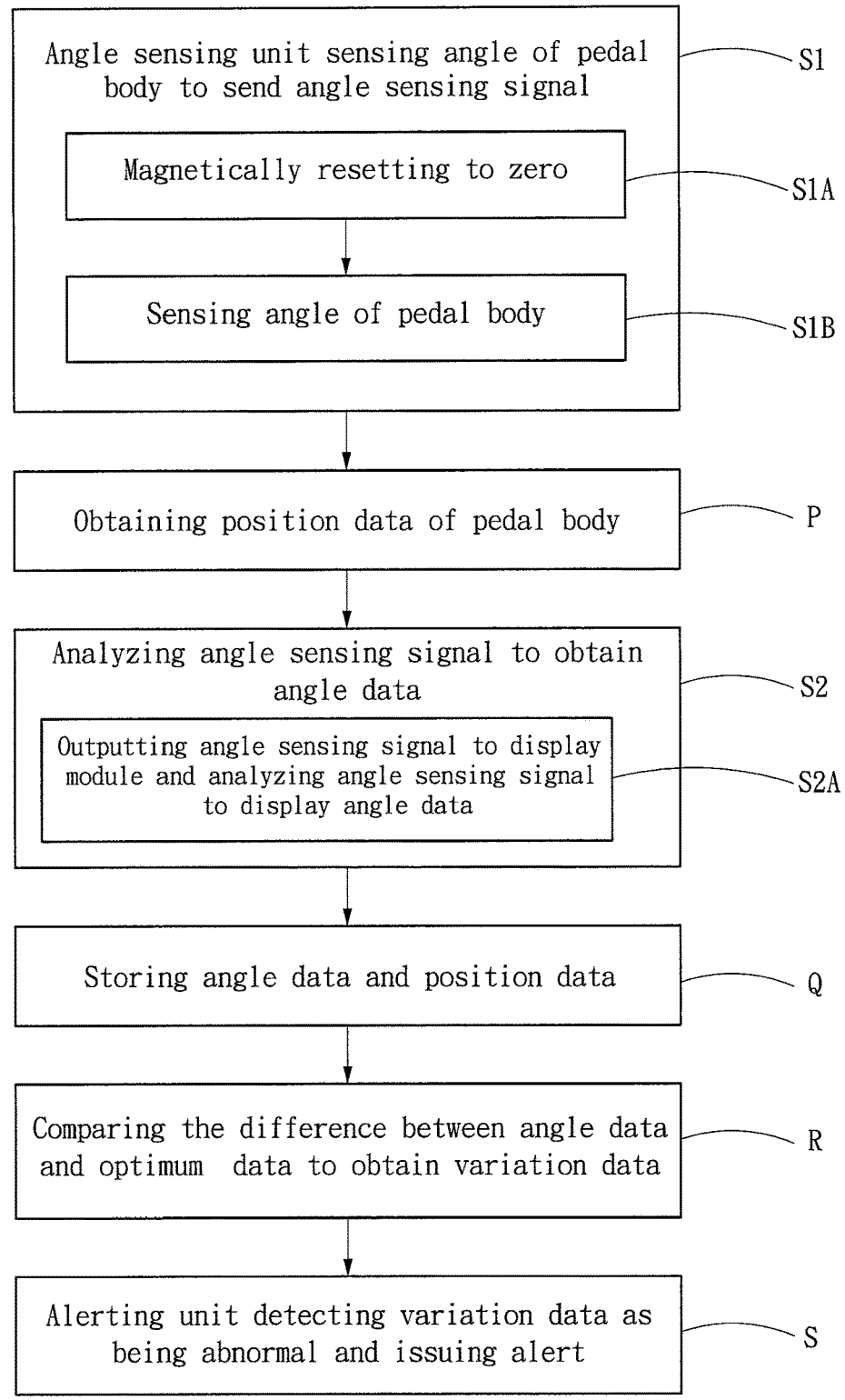
FIG. 9 is a schematic diagram of a process according to the second embodiment of the present invention.

FIG. 8 and FIG. 9 show a second embodiment of the present invention. One difference of the second embodiment from the first embodiment is that, this embodiment further includes a wireless transmission unit 50 and a display module 60. The wireless transmission unit 50 may wirelessly connect to the CPU 30 and the display module 60, and analyze the angle sensing signal through an application software 61 of the display module 60 to obtain the angle data. The angle data may be displayed on the display module 60. Further, the data stored in the data storage unit 40 may also be displayed on the display module 60 for the user to view.

In this embodiment, step S2 of the measuring method further includes following steps.

In step S2A, the CPU 30 wirelessly connects to the display module 60 through the wireless transmission unit 50, and analyzes the angle sensing signal through the application software 61 of the display module 60 to display the angle data on the display module 60.

Figure 10:
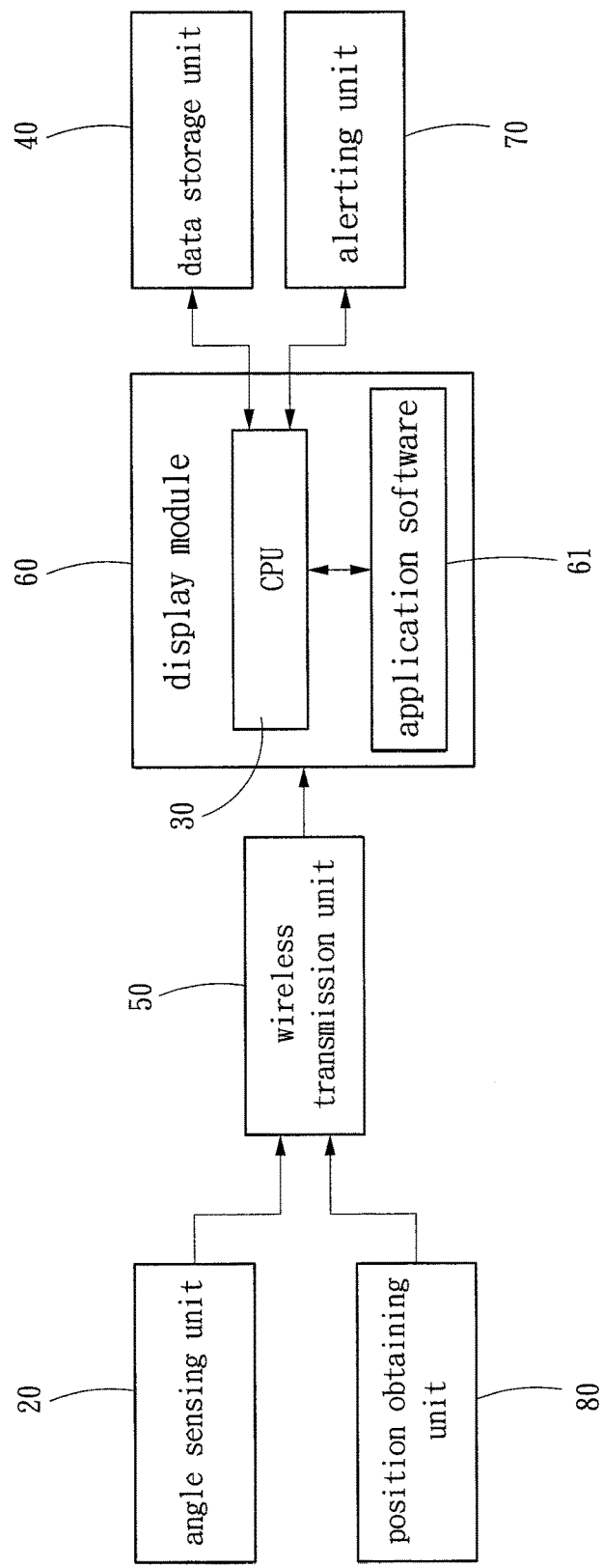
FIG. 10 is a function block diagram according to a third embodiment of the present invention.

FIG. 10 shows a third embodiment of the present invention. In this embodiment, the CPU 30 is disposed in a display module 60, and the wireless transmission unit 50 wirelessly connects to the CPU 30 and the angle sensing unit 20.

Further, the wireless transmission unit 50 transmits the angle sensing signal sent by the angle sensing unit 20 to the CPU 30. The angle sensing signal is analyzed through the application software 61, and the angle data is displayed on the display module 60.

In the second embodiment and the third embodiment of the present invention, the alerting unit 70 and the data storage unit 40 are disposed in the accommodating chamber 11 of the pedal body 10 as a non-limiting example. For another example, the alerting unit 70 and the data storage unit 40 may also be disposed in the display module 60.

In conclusion, the present invention provides following features.

1. The angle data may coordinate with other sensing data and be mutually corrected. For example, by mutually coordinating and correcting the angle data and pedaling force data of a pedaling force sensing unit, the correct pedaling force can be obtained.

2. By analyzing the angle data of the pedal body relative to the reference plane, it may be learned whether the pedaling angle during riding is correct. With further inspection of the angle data stored in the data storage unit, sports injuries can be reduced while enhancing riding efficiency.

3. With the alerting unit disposed, when the angle data is detected as being abnormal, the alerting unit issues an alert to notify the rider to pay attention to the pedaling posture to reduce sports injuries.

4. By analyzing the angle data of the pedal body relative to the reference plane, the effective force application direction along the tangential direction of the circumference can be obtained to further correct the pedaling angle of the rider, thereby optimizing the result of the pedaling force.

What is claimed is:

1. A measuring device for a pedal plane angle of a bicycle, which is pivotally connected to a mandrel, comprising:
    a pedal body, comprising a pivoting portion for pivotally connecting to the mandrel, a pedal plane, and an accommodating chamber;
    an angle sensing unit, disposed in the accommodating chamber;
    a central processing unit (CPU), electrically connected to the angle sensing unit; and
    a position obtaining unit, electrically connected to the CPU,
    wherein, the angle sensing unit senses an angle of the pedal body to send an angle sensing signal the position obtaining unit obtains and sends a position data according to a position of the pedal body performing a circular motion to the CPU, and the CPU analyzes the angle sensing signal to obtain an angle data of the pedal body relative to an angle of a reference plane and combines the angle data and the position data to obtain a pedaling motion information.

2. The measuring device for a pedal plane angle of a bicycle of claim 1, further comprising:
    a data storage unit, electrically connected to the CPU, storing the angle data.

3. The measuring device for a pedal plane angle of a bicycle of claim 1, further comprising:
    a wireless transmission unit, wirelessly connected to the CPU and the angle sensing unit;
    wherein, the CPU is disposed in a display module, the display module further comprises a application software, and the CPU analyzes the angle sensing signal through the application software to display the angle data.

4. The measuring device for a pedal plane angle of a bicycle of claim 1, further comprising:
    an alerting unit, electrically connected to the CPU, issuing an alert when the angle data is detected as being abnormal.

5. The measuring device for a pedal plane angle of a bicycle of claim 1, wherein the reference plane is a horizontal plane.

6. The measuring device for a pedal plane angle of a bicycle of claim 1, wherein the pedal body comprises a battery slot, and the mandrel and the battery slot are disposed between the pedal plane and the accommodating chamber.

7. The measuring device for a pedal plane angle of a bicycle of claim 1, wherein the angle sensing unit is at least one selected from a group consisting of an accelerometer, a gyroscope and an angle sensor.

8. A measuring method for a pedal plane angle of a bicycle, comprising steps of:
    S1: sensing an angle of a pedal body using an angle sensing unit disposed on the pedal body to send an angle sensing signal;
    P: obtaining a position data of a position of the pedal body performing a circular motion by a position obtaining unit; and
    S2: analyzing the angle sensing signal by a central processing unit (CPU) to obtain angle data of the pedal body relative to an angle of a reference plane and combining the angle data and the position data by the CPU to obtain a pedaling motion information.

9. The measuring method for a pedal plane angle of a bicycle of claim 8, wherein step S1 further comprises steps of:
    S1A: magnetically resetting the angle sensing unit to zero in response to magnetism differences in different regions; and
    S1B: sensing the angle of the pedal body by the angle sensing unit to send the angle sensing signal.

10. The measuring method for a pedal plane angle of a bicycle of claim 9, wherein in step S1A, the angle sensing unit is an angle sensor, and the angle sensing unit magnetically reset to zero by moving along a track of the numeral 8 in the air.

11. The measuring method for a pedal plane angle of a bicycle of claim 8, after step S2, further comprising a step of:
    Q: storing the angle data by a data storage unit.

12. The measuring method for a pedal plane angle of a bicycle of claim 8, after step S2, further comprising a step of:
    R: comparing the difference between the angle data and an optimum data by the CPU to obtain a variation data, wherein the optimum data is according to the consideration of ergonomics and the most effective riding angle.

13. The measuring method for a pedal plane angle of a bicycle of claim 12, after step R, further comprising a step of:
    S: issuing an alert by the alerting unit when the alerting unit detects the variation data as being abnormal.

14. The measuring method for a pedal plane angle of a bicycle of claim 8, wherein step S2 further comprises:
    S2A: the CPU wirelessly connecting to a display module through a wireless transmission unit, and analyzing the angle sensing signal through a application software of the display module to display the angle data.

* * * * *